(12) United States Patent
Kauffmann et al.

(10) Patent No.: US 11,994,517 B2
(45) Date of Patent: May 28, 2024

(54) ANALYTICAL ASSAY REACTION CARTRIDGE CONTAINING MAGNETIC CAPTURE BEADS AND METHODS OF PRODUCTION AND USE THEREOF

(71) Applicant: Siemens Healthcare Diagnostics Inc., Tarrytown, NY (US)

(72) Inventors: Aaron Kauffmann, Elkhart, IN (US); Jon Stradinger, Kalamazoo, MI (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 18/000,944

(22) PCT Filed: Jun. 16, 2021

(86) PCT No.: PCT/US2021/037599
§ 371 (c)(1),
(2) Date: Dec. 7, 2022

(87) PCT Pub. No.: WO2021/257682
PCT Pub. Date: Dec. 23, 2021

(65) Prior Publication Data
US 2023/0194513 A1  Jun. 22, 2023

Related U.S. Application Data

(60) Provisional application No. 63/040,867, filed on Jun. 18, 2020.

(51) Int. Cl.
*G01N 33/543* (2006.01)
*B01L 3/00* (2006.01)
*G01N 33/68* (2006.01)

(52) U.S. Cl.
CPC .. *G01N 33/54326* (2013.01); *B01L 3/502761* (2013.01); *G01N 33/54386* (2013.01);
(Continued)

(58) Field of Classification Search
None
See application file for complete search history.

(56) References Cited

U.S. PATENT DOCUMENTS

2006/0257958 A1  11/2006  Bruno
2014/0227679 A1  8/2014  Lee et al.
(Continued)

FOREIGN PATENT DOCUMENTS

WO  2009068027 A1  6/2009
WO  2015028769 A1  3/2015
(Continued)

OTHER PUBLICATIONS

Park, "A giant magnetoresistive reader platform for quantitative lateral flow immunoassays", Sensors and Actuators A: Physical, 250, pp. 55-59, available online Sep. 12, 2016. (Year: 2016).*
(Continued)

*Primary Examiner* — Rebecca M Giere

(57) ABSTRACT

Analytical assay reaction cartridges, kits containing same, and methods of production and use thereof are disclosed. These cartridges include a magnetic assembly that surrounds at least a portion of a sample read window on the cartridge. The cartridge also includes an analytical reagent positioned therewithin, wherein the analytical reagent comprises magnetic beads coated with at least one anti-red blood cell antibody.

26 Claims, 7 Drawing Sheets

(52) U.S. Cl.
CPC ...... *G01N 33/6872* (2013.01); *B01L 2200/04* (2013.01); *B01L 2200/0668* (2013.01); *B01L 2200/16* (2013.01); *B01L 2400/043* (2013.01); *G01N 2333/4737* (2013.01)

(56) References Cited

U.S. PATENT DOCUMENTS

| | | |
|---|---|---|
| 2017/0108495 A1 | 4/2017 | Ikeda et al. |
| 2017/0343466 A1 | 11/2017 | Dou et al. |
| 2019/0056384 A1 | 2/2019 | Gershtein et al. |

FOREIGN PATENT DOCUMENTS

| | | |
|---|---|---|
| WO | 2015191450 A1 | 12/2015 |
| WO | 2020251849 A1 | 12/2020 |

OTHER PUBLICATIONS

Kim et al., "Plastic-Chip-Based Magnetophoretic Immunoassay for Point-Of-Care Diagnosis of Tuberculosis", ACS Applied Materials & Interfaces, 8, pp. 23489-23497, published Aug. 22, 2016. (Year: 2016).*

International Search Report and Written Opinion of International Application No. PCT/US2021/037599 dated Sep. 15, 2021.

Liu et al., "Membrane-based, sedimentation-assisted plasma separator for point-of-care applications", Anal Chem. Nov. 5, 2013; 85(21): pp. 1-17.

\* cited by examiner

ANALYTICAL ASSAY REACTION CARTRIDGE CONTAINING MAGNETIC CAPTURE BEADS AND METHODS OF PRODUCTION AND USE THEREOF

CROSS REFERENCE TO RELATED APPLICATIONS/INCORPORATION BY REFERENCE STATEMENT

The subject application claims benefit under 35 USC § 119(e) of U.S. Provisional Application No. 63/040,867, filed Jun. 18, 2020. The entire contents of the above-referenced patent application(s) are hereby expressly incorporated herein by reference.

STATEMENT REGARDING FEDERALLY SPONSORED RESEARCH OR DEVELOPMENT

Not Applicable.

BACKGROUND

Numerous devices and methods exist for detecting analytes that may be present in a patient's biological liquid test sample. Such devices have been proven to be effective in diagnostic assays that detect the presence and/or quantity of certain analytes indicative of a patient's health, including, but not limited to, glycated hemoglobin (HbA1c), microalbumin and creatinine, and lipid-based analytes, such as (but not limited to) cholesterol, triglycerides, and/or high-density lipoproteins. These various analytical assays involve the use of analytical assay reaction cartridges that introduce at least one liquid analytical reagent within a reaction cartridge, that mixes with (and/or dilutes) the patient's biological liquid test sample as well as any solid analytical reagent(s) for performing the desired assay(s) that are also present in the reaction cartridge.

Currently available analytical assay systems such as the DCA VANTAGE® analyzer system commercially available from Siemens Healthineers, Inc. (Malvern, PA) are not capable of performing assays that require blood plasma as a specimen type using the existing fingerstick whole blood sampling method. The primary limiting factor in implementing these types of assays on such analyzers is the need to use either plasma or estimate hematocrit in a whole blood sample; this would require either (1) manually separating plasma from a blood sample before disposal in an analytical reaction cartridge, or (2) modifying the analyzer system to separate plasma and/or estimate hematocrit.

In addition, there are inaccuracies present in estimating hematocrit from a hemoglobin correlation, and multiple tags would be required to count red blood cells (RBCs) to reduce possible bias from abnormal cell types (such as, but not limited to, sickle cells), which have similar surface area (SA) but reduced cell volume (CV) when compared to a normal phenotype.

Therefore, there is a need in the art for new and improved analytical assay reaction cartridges, assemblies and kits containing same, and methods of producing and using these cartridges, assemblies, and kits, which allow for the measurement and distribution of RBCs and the performance of analytical assays for analytes present in plasma in a whole blood sample.

DETAILED DESCRIPTION

Figure 1:
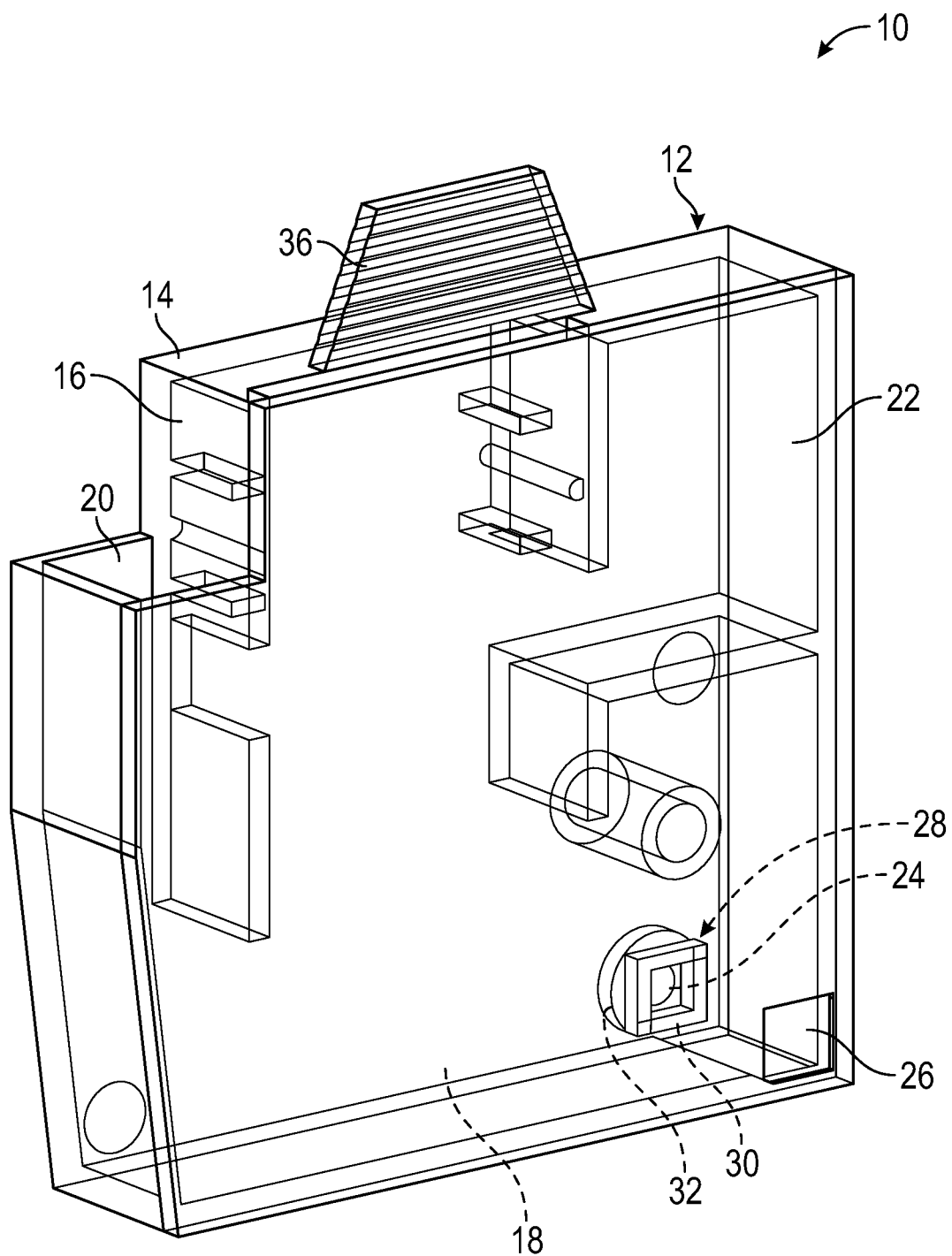
FIG. 1 is a transparent, perspective view of one non-limiting embodiment of an analytical assay reaction assembly constructed in accordance with the present disclosure and that includes an analytical assay reaction cartridge and a magnetic assembly.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions/devices, kits, and/or methods disclosed herein can be made and executed without undue experimentation in light of the present disclosure. While the compositions/devices, kits, and/or methods have been described in terms of particular embodiments, it will be apparent to those of skill in the art that variations may be applied to the compositions/devices, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

The use of ordinal number terminology (i.e., "first," "second," "third," "fourth," etc.) is solely for the purpose of differentiating between two or more items and, unless explicitly stated otherwise, is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps. For example, a process, method, article, or apparatus that comprises a list of elements is not necessarily limited to only those elements but may include other elements not expressly listed or inherently present therein.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the present disclosure. Examples of biological samples that may be utilized include, but are not limited to, whole blood or any portion thereof (i.e., plasma or serum), saliva, sputum, cerebrospinal fluid (CSF), intestinal fluid, intraperitoneal fluid, cystic fluid, sweat, interstitial fluid, tears, mucus, urine, bladder wash, semen, combinations thereof, and the like. The volume of the liquid test sample utilized in accordance with the present disclosure may be (for example but not by way of limitation) from about 0.1 µl to about 100 µl.

As used herein, the term "volume" as it relates to the liquid test sample utilized in accordance with the present disclosure means from about 0.1 µl to about 100 µl, or from about 1 µl to about 75 µl, or from about 2 µl to about 60 µl, or less than or equal to about 50 µl.

The term "patient" includes human and veterinary subjects. In certain embodiments, a patient is a mammal. In certain other embodiments, the patient is a human. "Mammal" for purposes of diagnosis/treatment refers to any animal classified as a mammal, including human, domestic and farm animals, nonhuman primates, and zoo, sports, or pet animals, such as dogs, horses, cats, cows, etc.

Turning now to particular non-limiting embodiments of the inventive concept(s), the present disclosure is related to improved device(s), assembly(ies), kit(s), and method(s) for performing analytical assays on blood cell-containing samples (such as, but not limited to, whole blood samples) using analytical assay reaction cartridges. Certain analyte assays cannot be performed with existing analytical assay reaction cartridges because of interference from red blood cells. For example, implementation of assays that require blood plasma as a specimen type (such as, but not limited to, C-Reaction Protein (CRP) assays) would require a manual plasma separation step prior to introduction of the sample into the reaction cartridge, or the analyzer system would need to be able to separate plasma and/or estimate hematocrit. However, there are inaccuracies present in estimating hematocrit from a hemoglobin correlation, and there is a need for multiple tags to count red blood cells (RBC) to reduce possible bias from abnormal cell types such as sickle cell, which has similar surface area (SA) but reduced cell volume (CV) when compared to a typical phenotype. The present disclosure describes a system that allows for the mechanical separation and/or optical correction of whole blood components in plasma, to enable the existing assay architecture to use whole blood in traditionally plasma or serum-only applications. In contrast to the currently available systems, the analytical assay reaction assemblies disclosed herein allow for the measurement of the distribution of RBC's after being tagged with magnetic capture beads and pulled against a read surface.

In certain non-limiting embodiments, the present disclosure is directed to an analytical assay reaction assembly that includes an analytical assay reaction cartridge, at least one solid analytical reagent that comprises magnetic beads, and a magnetic assembly. The analytical assay reaction cartridge has a housing that comprises a reaction chamber, an inlet for introducing a liquid test sample into the reaction chamber, and a sample read window formed through a portion of the reaction chamber, wherein the sample read window has an outer edge. The at least one solid analytical reagent comprises magnetic beads coated with at least one anti-human red blood cell antibody; in addition, the solid analytical reagent is soluble in a liquid reagent. The magnetic assembly comprises a permanent magnet. At least one contact point of the magnetic assembly is disposed substantially adjacent to at least one contact point on the outer edge of the sample read window of the analytical assay reaction cartridge.

The at least one solid analytical reagent may be disposed in any portion of the analytical assay reaction assembly that allows the assembly to function as described herein. In certain particular (but non-limiting) embodiments, the at least one solid analytical reagent is positioned within the reaction chamber of the analytical assay reaction cartridge.

The magnetic assembly may either be attached to the analytical assay reaction cartridge or be incorporated into a cartridge holder of a diagnostic instrument.

When the magnetic assembly is incorporated into the cartridge holder, the analytical assay reaction assembly further includes the cartridge holder, which is capable of receiving the analytical assay reaction cartridge. In this non-limiting embodiment, the magnetic assembly is attached to the cartridge holder such that the at least one contact point of the magnetic assembly is disposed substantially adjacent the at least one contact point on the outer edge of the sample read window of the analytical assay reaction cartridge when the analytical assay reaction cartridge is disposed within the cartridge holder.

In certain particular (but non-limiting) embodiments, the magnetic assembly further comprises an insulator member and at least one metal guide that connects the insulator member to the permanent magnet and extends through the insulator member to provide the at least one metal contact point on the outer surface of the insulator member that is disposed substantially adjacent to the at least one contact point on the outer edge of the sample read window of the analytical assay reaction cartridge.

When the magnetic assembly is attached to the analytical assay reaction cartridge, the at least one metal contact point of the magnetic assembly may be attached to the at least one contact point on the outer edge of the sample read window of the analytical assay reaction cartridge.

In certain particular (but non-limiting) embodiments, the magnetic assembly may include two or more metal guides that connect the insulator member to the permanent magnet and that extend through the insulator member to provide two or more metal contact points on the outer surface of the insulator member. When multiple metal contact points are present, each metal contact point is disposed substantially adjacent to a corresponding contact point on the outer edge of the sample read window of the analytical assay reaction cartridge.

The analytical assay reaction cartridge may further include a reagent tray that is disposed and retained within the housing. The reagent tray has a cavity formed therein to contain a predetermined volume of liquid reagent. The reagent tray also has a flexible cover removably attached thereto to seal the liquid reagent within the cavity and thereby form a sealed chamber between the cavity and the flexible cover. The flexible cover has a portion that extends beyond an upper end of the reagent tray and defines a tab portion which can be pulled to remove at least a portion of the flexible cover from the reagent tray and thereby release the liquid reagent into the reaction chamber of the housing.

In certain non-limiting embodiments, the analytical assay reaction cartridge further includes a predetermined volume of liquid reagent disposed within the cavity of the reagent tray. The at least one solid analytical reagent positioned within the reaction chamber is soluble in the liquid reagent disposed within the reagent tray.

In certain non-limiting embodiments, the analytical assay reaction cartridge further includes a capillary holder at least partially inserted into the inlet of the analytical assay reaction cartridge. The capillary holder functions to introduce a liquid test sample within the analytical assay reaction cartridge. The capillary holder includes a capillary that can be brought into contact with a liquid test sample such that a portion of the liquid test sample can be drawn into a capillary of the capillary holder; then the capillary holder can be disposed within at least a portion of the inlet of any of the analytical assay reaction cartridge to thereby introduce the liquid test sample into the reaction chamber of the analytical assay reaction cartridge.

The at least one solid analytical reagent may be positioned within the housing at any location and via any mechanism known in the art, so long as the analytical assay reaction cartridge is capable of accomplishing the functions in accordance with the present disclosure. For example (but not by way of limitation), the solid analytical reagent(s) may be simply positioned in an unattached form within the reaction chamber, or the solid analytical reagent(s) may be attached to a wall of the housing according to methods known in the art, such as by (for example and not by way of limitation) noncovalent binding techniques, absorptive techniques, and the like. For example (but not by way of limitation), the solid analytical reagent may be attached to a portion of the reaction chamber of the housing. Also, in one non-limiting embodiment, the solid analytical reagent is present in a substantially dry and water soluble (re-hydratable), re-suspendable, or re-dissolvable form. In one particular (but no-limiting) embodiment, the solid analytical reagent is in the form of a substantially flat, raised portion or mesa-shaped node on the surface of a selected area of the reaction chamber, in which the raised upper surface of each node is from about 0.005 inches to about 0.02 inches elevated above a surface of the reaction chamber.

The magnetic assembly may assume any configuration that allows the analytical assay reaction cartridge to function in accordance with the present disclosure. In one non-limiting embodiment, the magnetic assembly comprises an insulator member, a permanent magnet, and at least two metal guides that extend through the back member of the housing of the cartridge and connect the insulator member to the permanent magnet.

The insulator member may be formed of any non-ferrous material and may be provided with any size, shape, and/or configuration, so long as the insulator member does not interfere with the sample read window and allows the magnetic assembly to function in accordance with the present disclosure. Non-limiting examples of non-ferrous materials from which the insulator member may be formed include polyethylene, acrylic, soda-lime glass, aluminum, combinations thereof, and the like. In addition, a portion of the cartridge holder of the instrument may function as the insulator member, so long as said portion of the cartridge holder contains one or more openings through which the metal guides can be extended. The width of the insulator member can vary depending on the strength of the magnet; in certain non-limiting embodiments, the insulator member has a width of about 2 cm or less, about 1.5 cm or less, about 1 cm or less, about 0.9 cm or less, about 0.8 cm or less, about 0.7 cm or less, about 0.6 cm or less, about 0.5 cm or less, about 0.4 cm or less, about 0.3 cm or less, about 0.2 cm or less, about 0.1 cm or less, about 0.05 cm or less, about 0.01 cm or less, or the like. In addition, the insulator member may have a width that falls within a range of two of the above values (i.e., a range of from about 0.1 cm to about 1 cm, etc.).

Any permanent magnets known in the art that are capable of capturing the coated magnetic beads at a certain position within the analytical assay reaction cartridge may be utilized in accordance with the present disclosure. Non-limiting examples of permanent magnets that may be used in accordance with the present disclosure include one or more neodymium magnets, actuated electromagnets, alnico magnets, ferrite magnets, and the like. One particular (but non-limiting) example of a permanent magnet that can be utilized in accordance with the present disclosure includes a cylindrical neodymium magnet.

In addition, the magnet may be provided with any shape and/or size that allows the magnetic assembly to function as described herein. In certain non-limiting embodiments, the magnet is a cylindrical magnet that has a diameter in a range of from about 0.01 cm, about 0.02 cm, about 0.03 cm, about 0.04 cm, about 0.05 cm, about 0.06 cm, about 0.07 cm, about 0.08 cm, about 0.09 cm, about 0.1 cm, about 0.2 cm, about 0.3 cm, about 0.4 cm, about 0.5 cm, about 0.6 cm, about 0.7 cm, about 0.8 cm, about 0.9 cm, about 1 cm, about 1.5 cm, about 2 cm, about 2.5 cm, about 3 cm, about 3.5 cm, about 4 cm, about 4.5 cm, about 5 cm, about 5.5 cm, about 6 cm, about 6.5 cm, about 7 cm, about 7.5 cm, about 8 cm, about 8.5 cm, about 9 cm, about 9.5 cm, about 10 cm, or greater, as well as a range formed from any of the above values (i.e., a range of from about 0.01 cm to about 10 cm, a range of from about 0.1 cm to about 5 cm, etc.), and a range that combines two values that fall between two of the above-referenced values (i.e., a range of from about 0.035 cm to about 7.8 cm, etc.).

Any magnetic beads capable of being coated with at least one anti-human red blood cell antibody and capable of interacting with a magnetic assembly as described herein to capture red blood cells in a particular location within the analytical assay reaction cartridge may be utilized in accordance with the present disclosure. For example (but not by way of limitation), the magnetic beads can be any ferromagnetic beads that include iron, gold coated iron, polymer coated iron, or the like.

In addition, the magnetic beads may be provided with any shape and/or size that allows the magnetic beads to function as described herein. In certain non-limiting embodiments, the magnetic beads have a diameter in a range of from about 0.01 cm, about 0.02 cm, about 0.03 cm, about 0.04 cm, about 0.05 cm, about 0.06 cm, about 0.07 cm, about 0.08 cm, about 0.09 cm, about 0.1 cm, about 0.2 cm, about 0.3 cm, about 0.4 cm, about 0.5 cm, about 0.6 cm, about 0.7 cm, about 0.8 cm, about 0.9 cm, about 1 cm, about 1.5 cm, about 2 cm, about 2.5 cm, about 3 cm, about 3.5 cm, about 4 cm, about 4.5 cm, about 5 cm, about 5.5 cm, about 6 cm, about 6.5 cm, about 7 cm, about 7.5 cm, about 8 cm, about 8.5 cm, about 9 cm, about 9.5 cm, about 10 cm, or greater, as well as a range formed from any of the above values (i.e., a range of from about 0.01 cm to about 10 cm, a range of from about 0.1 cm to about 5 cm, etc.), and a range that combines two values that fall between two of the above-referenced values (i.e., a range of from about 0.035 cm to about 7.8 cm, etc.).

In a particular (but non-limiting) embodiment, the permanent magnet of the magnetic assembly is a cylindrical neodymium magnet that has a diameter in a range of from about 0.1 cm to about 5 cm, and the magnetic beads of the solid analytical reagent have a diameter of about 0.1 µm to about 5 µm.

The sample read window may be provided with any shape and/or size that allows any of the assays being performed in the analytical assay reaction cartridge to be read optically and that allows the analytical assay reaction cartridge to function in accordance with the present disclosure. For example (but not by way of limitation), the sample read window may have a shape that is circular, triangular, square, rectangular, pentagonal, hexagonal, heptagonal, octagonal, nonagonal, decagonal, hendecagonal, dodecagonal, or any shape with any number of sides capable of accomplishing the presently disclosed and/or claimed inventive concept(s).

In certain non-limiting embodiments, the sample read window is quadrilateral in shape, and the magnetic assembly comprises two metal guides and thus two metal contact points (which are formed by the portions of the two metal guides that extend through the insulator member). One metal contact point is disposed substantially adjacent or in contact with a contact point in an upper corner of the sample read window, while the other metal contact point is disposed substantially adjacent or in contact with a contact point in an opposing lower corner of the sample read window.

The analytical assay reaction cartridge may contain additional components or reagents that allow for one or more assays to be performed therein. As such, the analytical assay reaction cartridge may further include at least one additional liquid reagent and/or at least one additional solid analytical reagent. For example (but not by way of limitation), the analytical assay reaction cartridge may further include a second solid analytical reagent (which may be (for example, but not by way of limitation) positioned within the reaction chamber of the housing), wherein the second solid analytical reagent may be utilized in an assay for an analyte. In addition, any additional solid analytical reagent(s) should be soluble in the liquid reagent disposed in the reagent tray or in another liquid reagent disposed within the analytical assay reaction cartridge.

It is contemplated that virtually any reagent used in the fields of biological, chemical, or biochemical analyses and assays could be used in the devices, kits, and methods of the present disclosure. It is contemplated that, in certain non-limiting embodiments, these reagents may undergo physical and/or chemical changes when bound to an analyte of interest whereby the intensity, nature, frequency, and/or type of signal generated by the reagent-analyte complex is directly proportional or inversely proportional to the concentration of the analyte existing within the fluid sample. These reagents may contain (for example, but not by way of limitation) indicator dyes, metal, enzymes, polymers, antibodies, and electrochemically reactive ingredients and/or chemicals that, when reacting with an analyte(s) of interest, may exhibit a change in color. In addition, another non-limiting example of an analytical reagent is a buffer. In yet another, non-limiting example, the analytical reagent can be a solvent or solution in which a solid analytical reagent present in the reaction chamber can be dissolved or suspended.

Any method of detecting and/or measuring an analyte in a fluid sample can be used in the devices, kits, and methods of the present disclosure. A variety of assays for detecting analytes are well known in the art and include, but are not limited to, chemical assays, enzyme inhibition assays, antibody stains, latex agglutination, latex agglutination inhibition, and immunoassays such as (but not limited to) radioimmunoassays.

The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the present disclosure is not strictly limited to immunoassays and may include, by way of example and not by limitation, chemical and chemical-based assays, nucleic acid assays, lipid-based assays, and serology-based assays. Immunoassays (such as, but not limited to, radioimmunoassays and enzyme-linked immunoassays) are useful methods for use with the present disclosure. A variety of immunoassay formats, including, for example, competitive and non-competitive immunoassay formats, antigen/analyte capture assays, and two-antibody sandwich assays can be used in accordance with the cartridges, kits, and methods described herein. Enzyme-linked immunosorbent assays (ELISAs) can be used in accordance with the present disclosure as well. In the case of an enzyme immunoassay, an enzyme is typically conjugated to a second antibody, generally (for example but not by way of limitation) by means of glutaraldehyde, periodate, hetero-bifunctional crosslinking agents, or biotin-streptavidin complexes. As will be readily recognized, however, a wide variety of different conjugation techniques exist which are readily available for use with the present disclosure to one skilled in the art and thus are also included with the scope of the present disclosure.

In certain non-limiting embodiments, the analytical assay reaction cartridge includes a second solid analytical reagent for an assay that requires blood plasma as a specimen type. For example (but not by way of limitation), the second solid analytical agent may comprise beads coated with at least one anti-CRP (C-Reactive Protein) antibody.

Any additional solid analytical reagents present in the analytical assay reaction cartridge may be positioned within the reaction chamber of the housing at any location along the reaction chamber and via any mechanism known in the art, so long as the analytical assay reaction cartridge is capable of accomplishing the functions in accordance with the present disclosure. For example (but not by way of limitation), the additional solid analytical reagent(s) may be simply disposed in an unattached form within the reaction chamber, or the additional solid analytical reagent(s) may be attached to the back member or sidewall of the housing according to methods known in the art, such as by (for example and not by way of limitation) noncovalent binding techniques, absorptive techniques, and the like. Also, in one non-limiting embodiment, the additional solid analytical reagent(s) is present in a substantially dry and water soluble (re-hydratable), re-suspendable, or re-dissolvable form. In one particular (but no-limiting) embodiment, the additional solid analytical reagent(s) is in the form of a substantially flat, raised portion or mesa-shaped node on the surface of a selected area of the reaction chamber, in which the raised upper surface of each node is from about 0.005 inches to about 0.02 inches elevated above a surface of the reaction chamber.

In certain non-limiting embodiments, the housing of the analytical assay reaction cartridge further includes a flange extending from an upper perimeter side of the housing. This flange is utilized for positioning the analytical assay reaction cartridge within a diagnostic assay instrument.

Certain non-limiting embodiments of the present disclosure are directed to a method for performing at least one analytical reaction to determine the presence of an analyte in a liquid test sample using any of the analytical assay reaction assemblies described or otherwise contemplated herein. The method includes the steps of: (a) contacting a capillary holder with a liquid test sample, whereby a portion of the liquid test sample is drawn into a capillary of the capillary holder; (b) disposing the capillary holder within at least a portion of the inlet of the analytical assay reaction cartridge to thereby introduce the liquid test sample into the reaction chamber of the analytical assay reaction cartridge; (c) positioning the analytical assay reaction cartridge within a cartridge holder of a diagnostic assay instrument, wherein the predetermined volume of liquid reagent present in the cartridge is released from the reagent tray into the reaction chamber prior to, simultaneously with, or following insertion of the cartridge within the instrument, whereby the liquid reagent mixes with the liquid test sample and the solid analytical reagent to form a reaction mixture in the reaction chamber; and (d) measuring a detectable response in the reaction mixture through the sample read window of the cartridge to determine the presence of at least one analyte in the liquid test sample.

In certain non-limiting embodiments, in step (c), the liquid reagent is released from the reagent tray into the reaction chamber by pulling the tab portion of the flexible cover of the analytical assay reaction cartridge.

In certain non-limiting embodiments, the method further includes the step of rocking the analytical assay reaction cartridge following step (c) and prior to step (d), wherein the rocking is sufficient to allow the magnetic beads of the analytical reagent to pass by and accumulate over the magnetic assembly. For example (but not by way of limitation), the analytical assay reaction cartridge may be rocked at about 1 Hz to about 4 Hz over the magnetic assembly for a sufficient amount of time (such as, for example but not by way of limitation, a period in a range of from about 30 seconds to about 60 seconds) to pull all of the coated magnetic beads out of solution.

Certain non-limiting embodiments of the present disclosure are directed to a diagnostic assay instrument that has a cartridge holder that is capable of receiving an analytical assay reaction cartridge having a sample read window that has an outer edge. The cartridge holder comprises any of the magnetic assemblies disclosed or otherwise contemplated herein. When the analytical assay reaction cartridge is inserted in the cartridge holder, the at least one metal contact point of the magnetic assembly is disposed substantially adjacent at least one contact point on the outer edge of the sample read window of the analytical assay reaction cartridge. The diagnostic assay instrument may be a modified version of any diagnostic assay instruments known in the art or otherwise contemplated herein that are utilized with well-known analytical assay reaction cartridges/kits of similar format to those described and contemplated herein, such as (but not limited to) the DCA VANTAGE® analyzer system commercially available from Siemens Healthineers, Inc. (Malvern, PA).

Turning now to the Figures, FIG. 1 illustrates one non-limiting embodiment of the present disclosure, in which a magnetic assembly of an analytical assay reaction assembly is connected to the analytical assay reaction cartridge. The analytical assay reaction cartridge 10 includes a housing 12 that includes a back member 14, a sidewall 16 attached to the back member 14, and a lid member 22 attached to a portion of the sidewall 16. The housing 12 further includes a reaction chamber 18 defined by a lower portion of the housing 12. The housing 12 also includes an inlet 20 for introducing a liquid test sample into the reaction chamber 18; the inlet 20 is in fluidic communication with (or is capable of being in fluidic communication with) the reaction chamber 18. The inlet 20 is capable of securely receiving a capillary holder (such as, for example (but not by way of limitation) the capillary holder 102 of FIG. 2, as described in detail herein after) and is capable of introducing a liquid test sample from the capillary holder into the reaction chamber 18 of the cartridge 10.

The housing 12 may be constructed such that one or more of the components thereof (i.e., the back member 14, sidewall 16, and/or lid member 22) are integrally formed as one contiguous piece, for example (but not by way of limitation), one contiguous piece of plastic. Alternatively (and/or in addition thereto), one or more components of the housing 12 may be formed separately and then connected to one another via any method known in the art, such as (but not limited to) adhesive(s), glue, sonic welding, laser welding, and/or any type of permanent fastener(s).

The analytical assay reaction cartridge 10 further includes a sample read window 24 through the back member 14 and a corresponding sample read window 26 through the lid member 22 that together form a sample read window that is located at a position that contacts a portion of the reaction chamber 18. The sample read windows 24 and 26 can be, by way of example only and not by way of limitation, a transparent cuvette window or an optical window which permits the accurate measurement of detectable assay signals in the area of the sample read window 24/26.

Figure 3:
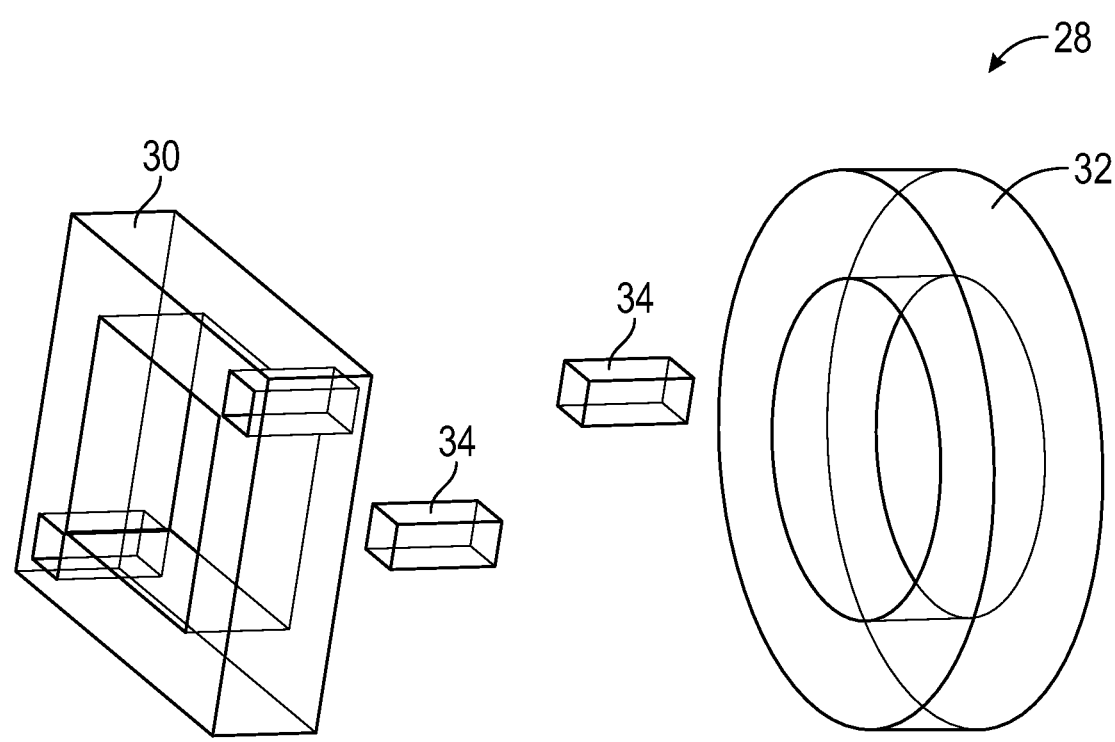
FIG. 3 is a transparent, perspective view of a magnetic assembly of the analytical assay reaction cartridge of FIG. 1.

The analytical assay reaction cartridge 10 further includes a magnetic assembly 28, as shown in FIGS. 1 and 3. The magnetic assembly 28 includes an insulator member 30 attached to the back member 14 at a position that substantially surrounds the sample read window 24 within the reaction chamber 18. The magnetic assembly 28 also includes a permanent magnet 32 that is indirectly connected to the back member 14 via two or more metal guides 34 (as shown in FIG. 3), at a position that substantially surrounds the sample read window 24. The insulator member 30 and the permanent magnet 32 are connected to one another via two or more metal guides 34, as shown in FIG. 3.

In certain non-limiting embodiments, the permanent magnet 32 is disposed outside of the housing 12. The metal guides 34 are sized and shaped so as to connect the permanent magnet 32 to the insulator member 30 in a manner that provides a space between the permanent magnet 32 and the back member 14 of the housing 12; in particular (but non-limiting) embodiments, the permanent magnet 32 and the back member 14 of the housing 12 have a space therebetween of about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, as well as a range of two of the above values (i.e., a range of from about 1 mm to about 10 mm, etc.).

In certain non-limiting embodiments, the housing 12 of the cartridge 10 further includes a flange 36 that generally extends from (for example, but not by way of limitation) an upper portion of the housing 12.

Figure 2:
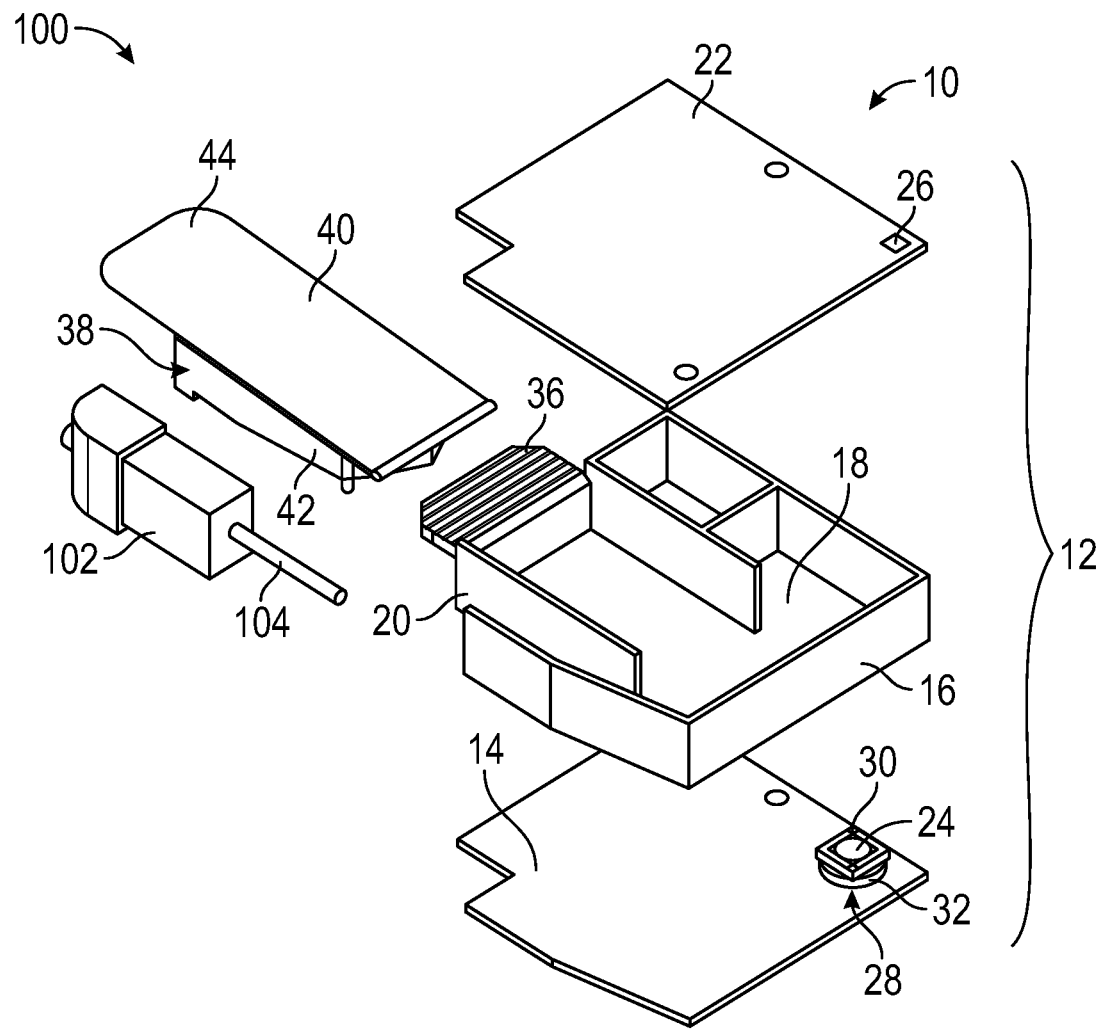
FIG. 2 is an exploded perspective view of one non-limiting embodiment of an analytical assay reaction kit containing the analytical assay reaction cartridge of FIG. 1.

FIG. 2 illustrates an analytical assay reaction kit that includes the analytical assay reaction cartridge 10 of FIG. 1 in combination with a reagent tray 38 and a capillary holder 102 and capillary 104.

The reagent tray 38 is disposed, affixed, and secured in place within the housing 12. The reagent tray 38 may be secured in place by any methods disclosed herein, including (but not limited to) a bonding material or a frictional engagement. The reagent tray 38 has a cavity 42 in which a predetermined volume of liquid reagent can be disposed. A flexible cover 40 is removably attached to an upper edge of the reagent tray 38 to seal liquid reagent within the cavity 42 of the reagent tray 38 and thereby form a sealed chamber between the cavity 42 and the flexible cover 38. In addition, the flexible cover 40 has a portion that extends beyond the reagent tray 38 and defines a tab portion 44 which can be pulled to remove a portion or all of the flexible cover 40 from the reagent tray 38 and thereby release the liquid reagent from the reagent tray 38 by allowing for the gravitational dispensing and flow of the liquid reagent into the reaction chamber 18 of the housing 12.

The lid member 22 is sealed to at least a portion of the sidewall 16 of the housing 12 so as to seal the reagent tray 38 within the housing 12. Such seal can be accomplished via any method commonly known in the art, such as (but not limited to) adhesive(s), glue, sonic welding, laser welding, and/or any type of permanent fastener(s), or simply via frictional engagement.

Figure 4:
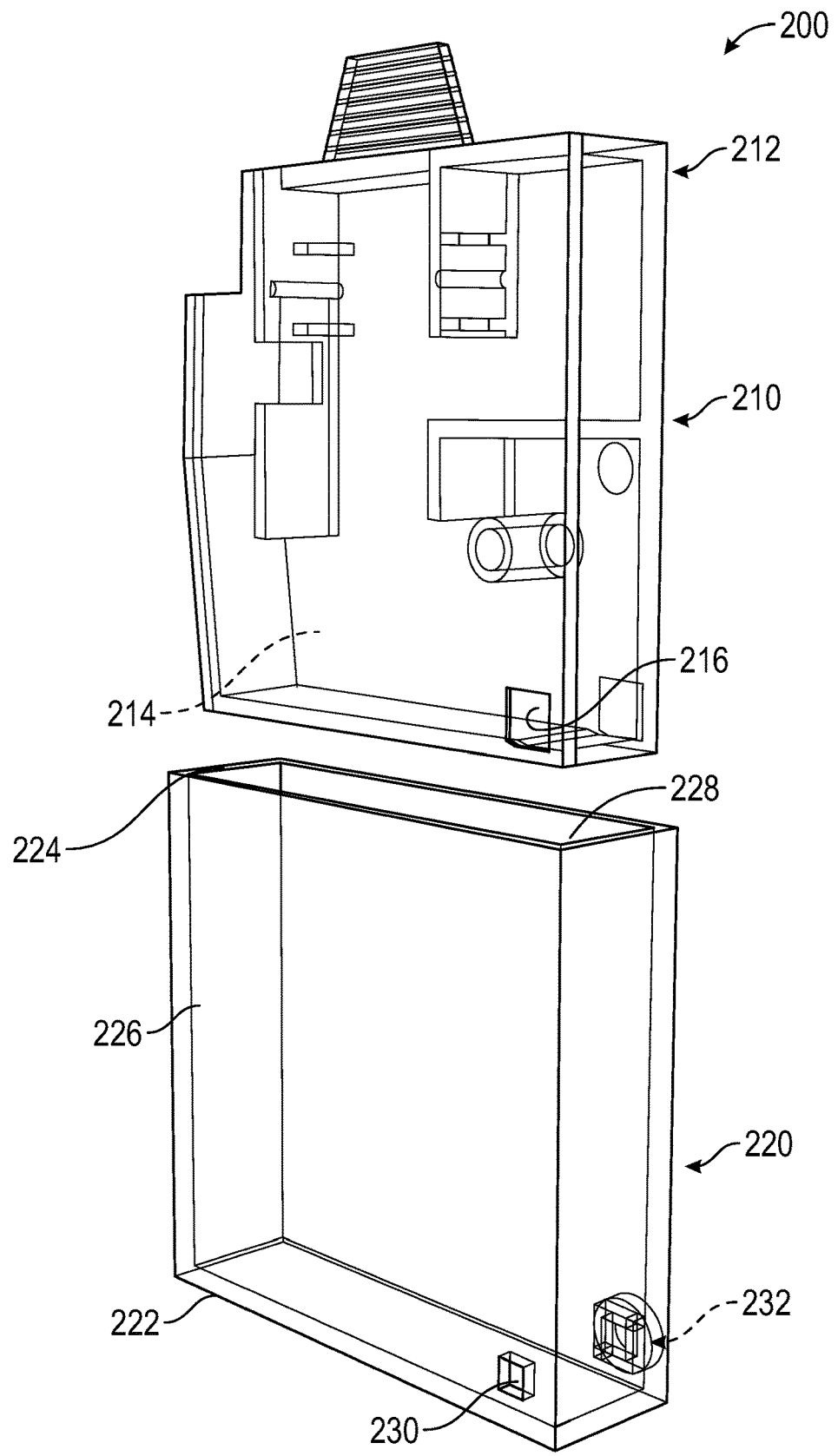
FIG. 4 contains a perspective view of one non-limiting embodiment of an analytical assay reaction assembly constructed in accordance with the present disclosure and that includes an analytical assay reaction cartridge and a cartridge holder having a magnetic assembly.

FIG. 4 illustrates another non-limiting embodiment of the present disclosure, in which the magnetic assembly of the analytical assay reaction assembly is connected to a cartridge holder of a diagnostic instrument into which an analytical assay reaction cartridge is disposed. The analytical assay reaction assembly is indicated by the general reference numeral 200 and includes an analytical assay reaction cartridge 210 and a cartridge holder 220 having a magnetic assembly 232 attached thereto. The analytical assay reaction cartridge 210 is similar to the analytical assay reaction cartridge 10 of FIGS. 1-2 (with the exception that a magnetic assembly is not attached thereto) and includes a housing 212 that includes a reaction chamber 214 and a sample read window 216. The cartridge holder 220 has a lower end 222, an open upper end 224, and a sidewall 226 that defines a receiving space 228 sized and dimensioned to receive the analytical assay reaction cartridge 210. The cartridge holder 220 also includes a sample read window 230 that aligns with the sample read window 216 of the analytical assay reaction cartridge 210. A magnetic assembly 232 that is similar to the magnetic assembly 28 of FIGS. 1-3 is disposed about and/or attached to the sample read window 230 of the cartridge holder 220.

Example

An Example is provided hereinbelow. However, the present disclosure is to be understood to not be limited in its application to the specific experimentation, results, and laboratory procedures disclosed herein after. Rather, the Example is simply provided as one of various embodiments and is meant to be exemplary, not exhaustive.

In this Example, a magnetic assembly is embedded in an analytical assay reaction cartridge (such as, but not limited to, a DCA Cartridge) along the back exterior thereof, as shown in FIGS. 1-2. The metal guides on the magnetic assembly will be in contact with the cartridge (and extend through the back member thereof). Red blood cells predominantly collect along the metal contacts and not with the configuration of the permanent magnet behind them due to the inverse cube law of electromagnetic fields. The distance between the magnet and the back member of the cartridge may be in a range of from about 1 mm to about 10 mm.

If a metal heating plate design is used, a portion surrounding the magnet should be removed to facilitate control of the field; should this not be possible, as long as the magnet is in contact with two points on either side of the sample read window (metal plate or not), the inverse cube law will maintain the magnetic field locally to where it is applied.

The magnetic assembly utilized in this Example is shown in an exploded view in FIG. 3. The plastic insulator and permanent magnet may be provided with any configuration (such as, but not limited to, square, circular, oblong, rectangular, etc.), so long as they perform their functions of insulation and/or magnetic field source, without interfering with the optical path. In a similar manner, the metal guides may be provided with any configuration (such as, but not limited to, cylindrical, cubic, short, long, wide, etc.), so long as they perform their function of accumulating ferric material along opposing corners of the optical window (such as, but not limited to, the bottom left and/or top right of the optical window based on the configuration illustrated in FIG. 3).

Figure 5:
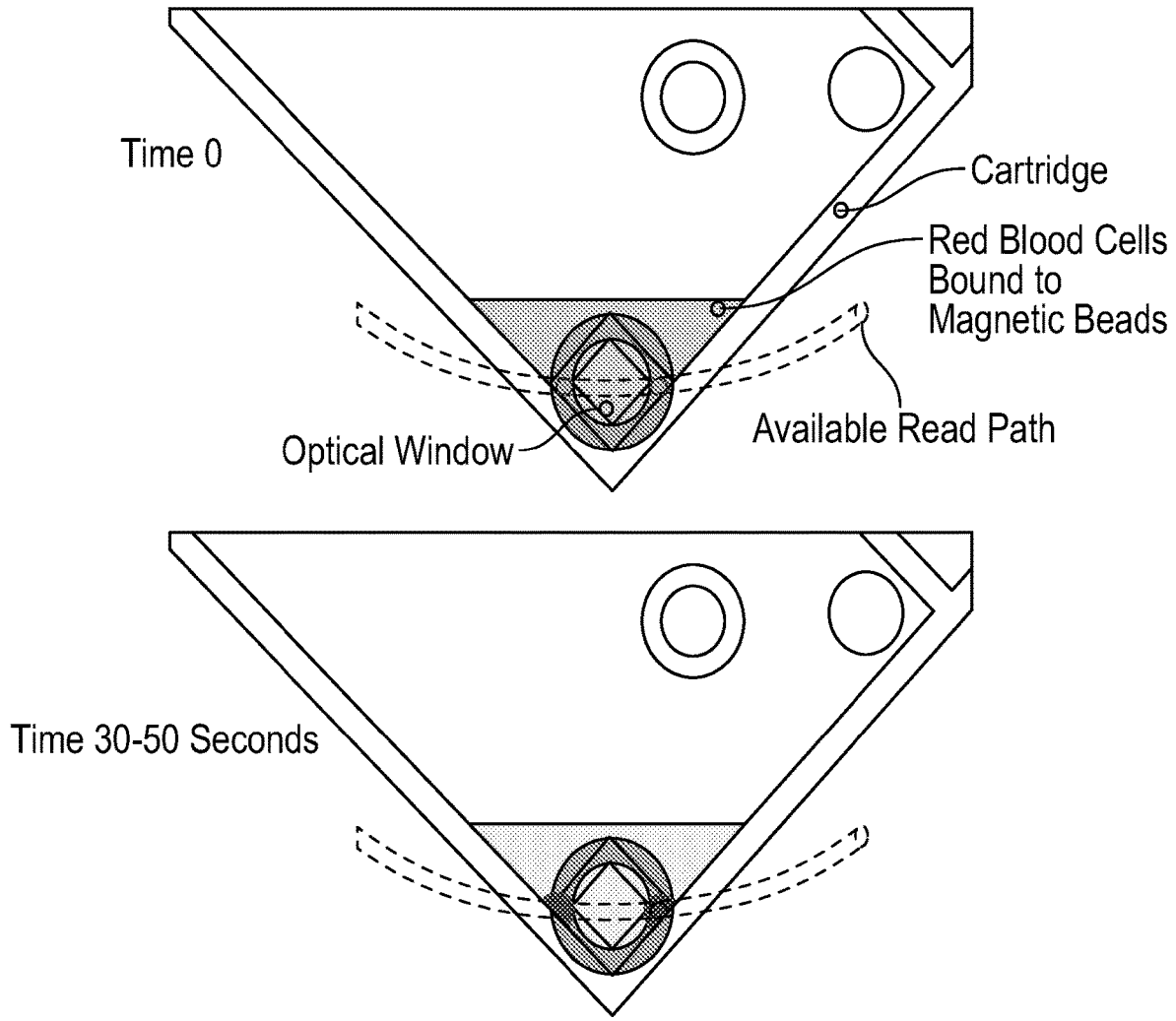
FIG. 5 contains a perspective view of a portion of the analytical assay reaction cartridge of FIG. 1 in use.

Regardless of the configuration of the analytical assay reaction assembly (i.e., the magnetic assembly attached to the cartridge or the cartridge holder), the use of the analytical assay reaction assembly is the same. After a sample has been added to the cartridge, the buffer tab pulled, the buffer blanked, and the sample mixed with the magnetic anti-human RBC beads, the sample moves over the magnetic portion of the cartridge. The solution rocks at a frequency in a range of from about 1 Hz to about 4 Hz over the magnet for sufficient period of time (such as, but not limited to, about 30 seconds to about 50 seconds) to pull all of the ferric material out of solution, as shown in FIG. 5. The distance the beads spread over the surface of the cartridge should be dependent on cell volume (hematocrit) and independent of cell surface area, thereby reducing any bias that may be associated with sickle cell, which presents with similar surface area but different cell volume than normal red blood cells. At this point, cell lysis can also be estimated by comparing hematocrit to free hemoglobin.

After hematocrit is estimated, plasma volume can be determined so long as the initial sample volume is known. The plasma in solution may then be reacted with the remaining set of analytical assay reagent(s) (i.e., reagent mesas). The remaining mesas vary widely and may range from anti-CRP beads for a CRP agglutination assay to some reagent indicator with digitonin that may be used to lyse the already captured RBC.

Table 1 below provides exemplary reagent formulations for the solid analytical assay reagent containing anti-RBC coating magnetic beads, a second solid analytical assay reagent that includes an anti-CRP reagent, and a buffer (i.e., liquid reagent) for dissolving the two solid analytical assay reagents.

TABLE 1

Example Reagent Formulations

| Reagent | Dispense Volume | Formulation |
| --- | --- | --- |
| RBC Magnetic Beads | 10-15 µL | 4% Dissolved Solids* |
|  |  | 0.75% BSA |
|  |  | 0.25% Gelatin |
|  |  | 10 mM Glycine |
|  |  | 7.5% Sucrose |
|  |  | 7.5% Trehalose |
|  |  | pH 9.3 |
| Buffer | 600 µL | NaCl |
|  |  | KCl |
|  |  | $Na_2HPO_4$ |
|  |  | $KH_2PO_4$ |
| Anti-CRP Latex | 10-15 µL | 5% Dissolved Solids* |
|  |  | 0.75% BSA |
|  |  | 0.25% Gelatin |
|  |  | 10 mM Glycine |
|  |  | 7.5% Sucrose |
|  |  | 7.5% Trehalose |
|  |  | pH 9.3 |

*Dependent on a 1 µL whole blood sample. More sample = more solids, with surface area being the limiting factor. Using modified Advia CRP_2 polyclonal rabbit antibody.

Figure 6:
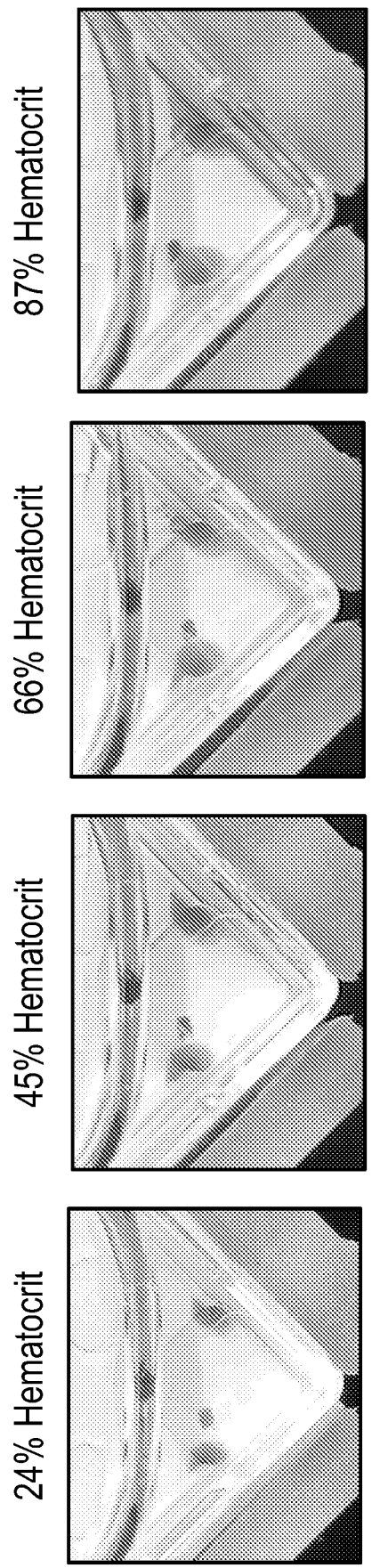
FIG. 6 contains images demonstrating separation of red blood cells in the analytical assay reaction cartridge of FIG. 1 at various hematocrit percentages.

FIG. 6 provides an example of manual collection of RBCs using a magnetic assembly constructed in accordance with the present disclosure. The images of FIG. 6 were made using a locally collected blood draw, EasySep™ RBC Depletion Reagent (Stemcell Technologies, Cambridge, MA; PN: 18170), DCA ACR (albumin, creatinine and albumin/creatinine ratio) cartridges (Siemens Healthineers, Inc., Malvern, PA), PBS, and a custom printed holder. The blood draw was gently mixed and spun on a CritSpin™ microhematocrit centrifuge (Beckman Coulter, Brea, CA) to obtain an initial hematocrit of 45%. From this stock, the dilution series shown in Table 2 was used to obtain the concentrations illustrated in FIG. 6 in an equivalent 1 µL sample to 600 µL buffer.

TABLE 2

Sample Dilutions

| % Hematocrit | 24% | 45% | 66% | 87% |
| --- | --- | --- | --- | --- |
| Buffer to add | 9.99 ml | 9.98 ml | 9.98 ml | 9.97 ml |
| Sample to add | 8.33 µl | 16.67 µl | 25.00 µl | 33.33 µl |

Running one sample at a time, 600 µL of each mixture was added to a new cartridge, making sure not to dissolve present reagent. 1 µL of magnetic anti-RBC beads was added to each cartridge. Samples 24%, 45%, 66%, and 87% hematocrit were left to incubate in a refrigerator for 30, 60, 90, and 120 minutes, respectively. The addition of more material at each level required more time to separate, and images were then acquired. The extended time to separation required in this Example was due to the magnets contacting the cartridge through 1 cm long screws, decreasing their local strength. The time to separation can be adjusted by various factors, such as (but not limited to) decreasing the magnet/sample distance, increasing bead size, increasing temperature, utilizing a greater level of mixing, utilizing stronger magnets, utilizing more beads, etc.

Figure 7:
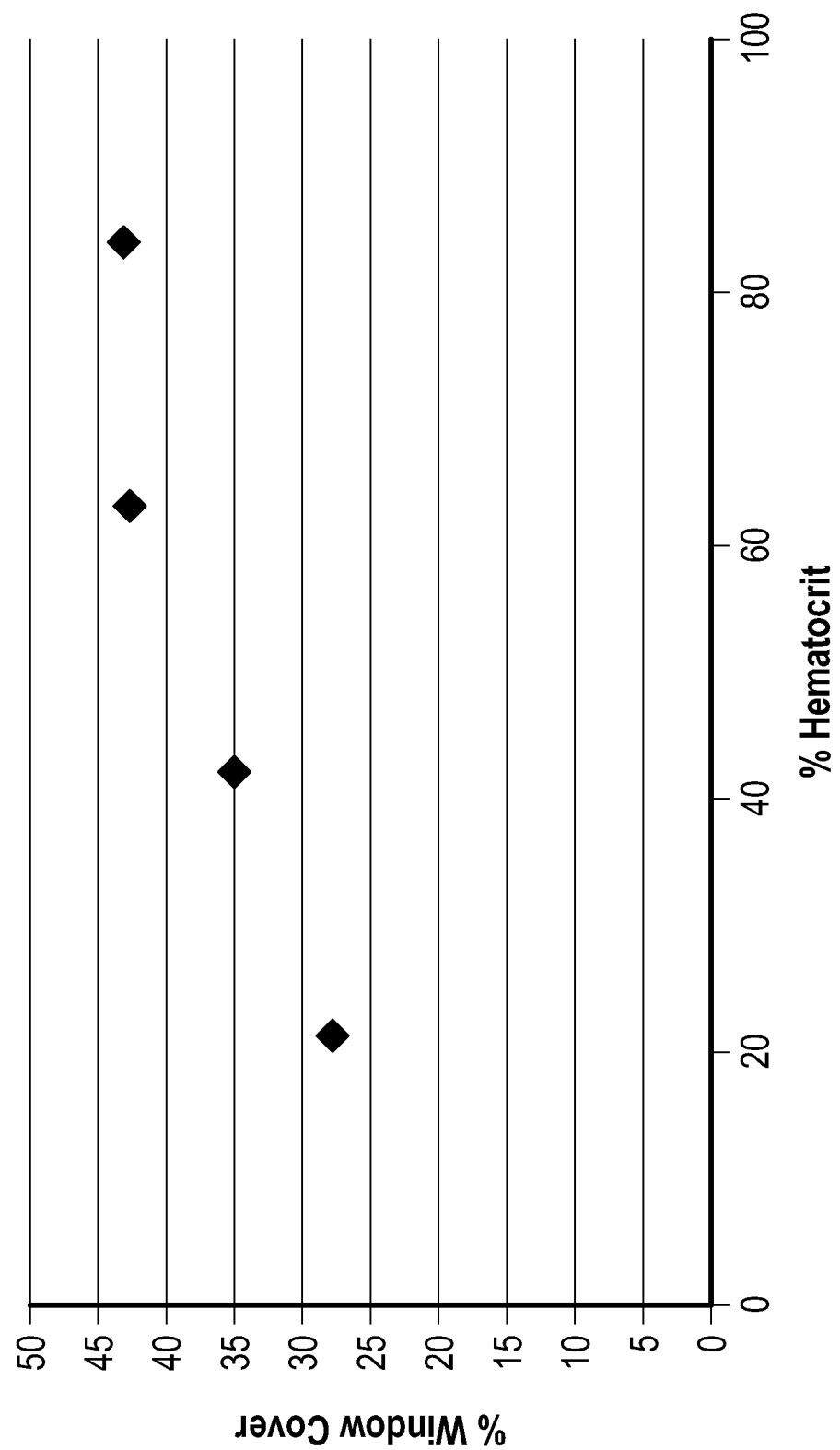
FIG. 7 is a graph of the data obtained from the images of FIG. 6.

FIG. 7 graphically illustrates use of the data collected using the images of FIG. 6, measuring horizontally across the read window and comparing this distance to the combined distance toward the center of either blood spot from the interior window of the cartridge. A linear correlation between the sample distribution and sample hematocrit is obtained for the expected population range of about 20% to about 60% hematocrit. While the linear correlation is not seen at 80% hematocrit, this is believed to be the result of an insufficient amount of magnetic beads being present. As such, a linear correlation below 20% hematocrit and above 80% hematocrit should be obtainable by adjusting one or more of the parameters discussed herein above.

Thus, in accordance with the present disclosure, there have been provided compositions/devices and kits, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. An analytical assay reaction assembly, comprising:
   an analytical assay reaction cartridge having a housing that comprises a reaction chamber, an inlet for introducing a liquid test sample into the reaction chamber, and a sample read window formed through a portion of the reaction chamber, wherein the sample read window has a shape with an outer edge that surrounds the shape of the sample read window that extends through the portion of the reaction chamber;
   at least one solid analytical reagent, wherein the solid analytical reagent comprises magnetic beads coated with at least one anti-human red blood cell antibody, and wherein the solid analytical reagent is soluble in a liquid reagent; and
   a magnetic assembly comprising a permanent magnet; and
   wherein at least one contact point of the magnetic assembly is disposed substantially adjacent to at least one contact point on the outer edge of the sample read window of the analytical assay reaction cartridge.

2. The analytical assay reaction assembly of claim 1, wherein the magnetic assembly is attached to the analytical assay reaction cartridge.

3. The analytical assay reaction assembly of claim 1, further comprising a cartridge holder of a diagnostic instrument, wherein the cartridge holder is capable of receiving the analytical assay reaction cartridge, and wherein the magnetic assembly is attached to the cartridge holder such that the at least one contact point of the magnetic assembly is disposed substantially adjacent to the at least one contact point on the outer edge of the sample read window of the analytical assay reaction cartridge when the analytical assay reaction cartridge is disposed within the cartridge holder.

4. The analytical assay reaction assembly of claim 1, wherein the magnetic assembly further comprises an insulator member and at least one metal guide that connects the insulator member to the permanent magnet and extends through the insulator member to provide at least one metal contact point on the outer surface of the insulator member that forms the at least one contact point of the magnetic assembly and that is disposed substantially adjacent to the at least one contact point on the outer edge of the sample read window of the analytical assay reaction cartridge.

5. The analytical assay reaction assembly of claim 4, wherein the magnetic assembly is attached to the analytical assay reaction cartridge, whereby the at least one metal contact point of the magnetic assembly is attached to the at least one contact point on the outer edge of the sample read window of the analytical assay reaction cartridge.

6. The analytical assay reaction assembly of claim 4, wherein the magnetic assembly comprises at least two metal guides that connect the insulator member to the permanent magnet and that extend through the insulator member to provide at least two metal contact points on the outer surface of the insulator member, and wherein the at least two metal contact points are each disposed substantially adjacent to a contact point on the outer edge of the sample read window of the analytical assay reaction cartridge.

7. The analytical assay reaction assembly of claim 4, wherein the sample read window of the analytical assay reaction cartridge is quadrilateral in shape, and the magnetic assembly comprises two metal guides, wherein the two metal guides form two contact points of the magnetic assembly, wherein one contact point is disposed substantially adjacent or in contact with a contact point in an upper corner of the sample read window and the other contact point is disposed substantially adjacent or in contact with a contact point in an opposing lower corner of the sample read window.

8. The analytical assay reaction assembly of claim 1, wherein the at least one solid analytical reagent is positioned within the reaction chamber of the analytical assay reaction cartridge.

9. The analytical assay reaction assembly of claim 8, wherein the solid analytical reagent is attached to a portion of the reaction chamber of the housing.

10. The analytical assay reaction assembly of claim 1, wherein the permanent magnet of the magnetic assembly is selected from the group consisting of a neodymium magnet, an actuated electromagnet, an alnico magnet, and a ferrite magnet.

11. The analytical assay reaction assembly of claim 1, wherein the permanent magnet comprises a cylindrical neodymium magnet that has a diameter in a range of from about 0.1 cm to about 5 cm, and wherein the magnetic beads of the solid analytical reagent have a diameter of about 0.1 µm to about 5 µm.

12. The analytical assay reaction assembly of claim 1, further comprising a second solid analytical reagent utilized in an assay for an analyte, wherein the solid analytical reagent is soluble in a liquid reagent.

13. The analytical assay reaction assembly of claim 12, wherein the second solid analytical reagent is positioned within the reaction chamber of the analytical assay reaction cartridge.

14. The analytical assay reaction assembly of claim 12, wherein the second solid analytical reagent comprises beads coated with at least one anti-CRP (C-Reactive Protein) antibody.

15. The analytical assay reaction assembly of claim 1, wherein the analytical assay reaction cartridge further comprises a flange extending from the housing.

16. The analytical assay reaction assembly of claim 1, further comprising:
    a reagent tray disposed and retained within the housing of the analytical assay reaction cartridge, the reagent tray having a cavity formed therein in which a predetermined volume of liquid reagent is disposed, the reagent tray having a flexible cover removably attached thereto that seals the liquid reagent within the cavity, wherein the flexible cover has a tab portion for releasing the liquid reagent into the reaction chamber of the housing, and wherein the solid analytical reagent is soluble in the liquid reagent; and
    a capillary holder at least partially inserted into the inlet of the analytical assay reaction cartridge.

17. A method for performing at least one analytical reaction to determine the presence of an analyte in a liquid test sample using the analytical assay reaction assembly of claim 16, the method comprising the steps of:
    (a) contacting the capillary holder with a liquid test sample, whereby a portion of the liquid test sample is drawn into a capillary of the capillary holder;
    (b) disposing the capillary holder within at least a portion of the inlet of the analytical assay reaction cartridge to thereby introduce the liquid test sample into the reaction chamber of the analytical assay reaction cartridge;
    (c) positioning the analytical assay reaction cartridge within a cartridge holder of a diagnostic assay instrument, wherein the predetermined volume of liquid reagent is released from the reagent tray into the reaction chamber prior to, simultaneously with, or following insertion of the cartridge within the diagnostic assay instrument, whereby the liquid reagent mixes with the liquid test sample and the solid analytical reagent to form a reaction mixture in the reaction chamber; and
    (d) measuring a detectable response in the reaction mixture through the sample read window of the cartridge to determine the presence of at least one analyte in the liquid test sample.

18. The method of claim 17, wherein in step (c), the liquid reagent is released from the reagent tray into the reaction chamber by pulling the tab portion of the flexible cover of the analytical assay reaction cartridge.

19. The method of claim 17, further comprising the step of rocking the analytical assay reaction cartridge following step (c) and prior to step (d), wherein the rocking is sufficient to allow the magnetic beads of the analytical reagent to pass by and accumulate over the magnetic assembly.

20. The method of claim 17, wherein the magnetic assembly is attached to the analytical assay reaction cartridge.

21. The method of claim 17, wherein the magnetic assembly is attached to the cartridge holder such that the at least one metal contact point of the magnetic assembly is disposed substantially adjacent to the at least one contact point on the outer edge of the sample read window of the analytical assay reaction cartridge.

22. The method of claim 17, wherein the magnetic assembly further comprises an insulator member and at least one metal guide that connects the insulator member to the permanent magnet and extends through the insulator member to provide at least one metal contact point on the outer surface of the insulator member that forms the at least one contact point of the magnetic assembly and that is disposed substantially adjacent to the at least one contact point on the outer edge of the sample read window of the analytical assay reaction cartridge.

23. The method of claim 22, wherein the magnetic assembly is attached to the analytical assay reaction cartridge, whereby the at least one metal contact point of the magnetic assembly is attached to the at least one contact point on the outer edge of the sample read window of the analytical assay reaction cartridge.

24. The method of claim 22, wherein the magnetic assembly comprises at least two metal guides that connect the insulator member to the permanent magnet and that extend through the insulator member to provide at least two metal contact points on the outer surface of the insulator member, and wherein the at least two metal contact points are each disposed substantially adjacent to a contact point on the outer edge of the sample read window of the analytical assay reaction cartridge.

25. The method of claim 17, wherein the permanent magnet of the magnetic assembly comprises a cylindrical neodymium magnet.

26. The method of claim 25, wherein the cylindrical neodymium magnet has a diameter in a range of from about 0.1 cm to about 5 cm, and wherein the magnetic beads of the solid analytical reagent have a diameter of about 0.1 µm to about 5 µm.

* * * * *